(12) United States Patent
Neuvonen et al.

(10) Patent No.: US 10,173,049 B2
(45) Date of Patent: Jan. 8, 2019

(54) STIMULATION ELECTRODE

(71) Applicant: Sooma Ltd., Helsinki (FI)

(72) Inventors: Tuomas Neuvonen, Espoo (FI); Jani Virtanen, Söderkulla (FI); Mika Nikander, Helsinki (FI)

(73) Assignee: Sooma Ltd., Helsinki (FI)

( * ) Notice: Subject to any disclaimer, the term of this patent is extended or adjusted under 35 U.S.C. 154(b) by 0 days.

(21) Appl. No.: 15/310,742

(22) PCT Filed: May 13, 2015

(86) PCT No.: PCT/EP2015/060660
§ 371 (c)(1),
(2) Date: Nov. 11, 2016

(87) PCT Pub. No.: WO2015/173335
PCT Pub. Date: Nov. 19, 2015

(65) Prior Publication Data
US 2017/0080208 A1 Mar. 23, 2017

(30) Foreign Application Priority Data
May 14, 2014 (EP) .................................. 14168306

(51) Int. Cl.
*A61N 1/00* (2006.01)
*A61N 1/04* (2006.01)
*A61N 1/20* (2006.01)

(52) U.S. Cl.
CPC ......... *A61N 1/0496* (2013.01); *A61N 1/0404* (2013.01); *A61N 1/0456* (2013.01); *A61N 1/205* (2013.01)

(58) Field of Classification Search
CPC .................. A61N 1/0404–1/0496; A61N 1/18
See application file for complete search history.

(56) References Cited

U.S. PATENT DOCUMENTS

| | | | |
|---|---|---|---|
| 5,205,297 A | 4/1993 | Montecalvo | |
| 2004/0087671 A1 | 5/2004 | Tamada | |
| 2011/0112607 A1 | 5/2011 | Zierhofer | |
| 2014/0046423 A1* | 2/2014 | Rajguru | A61N 1/0456 607/144 |

(Continued)

FOREIGN PATENT DOCUMENTS

| | | |
|---|---|---|
| EP | 0409067 A2 | 1/1991 |
| EP | 2055347 A1 | 5/2009 |

OTHER PUBLICATIONS

WIPO, International Preliminary Examining Authority (European Patent Office), International Preliminary Report on Patentability dated Aug. 29, 2015 in International Patent Application No. PCT/EP2015/060660, 12 pages.

(Continued)

*Primary Examiner* — Scott Getzow
(74) *Attorney, Agent, or Firm* — Inskeep IP Group, Inc.

(57) ABSTRACT

A skin electrode for stimulation comprising a superporous hydrophilic material having a first relaxed state and a second expanded state. In the second expanded state the superporous hydrophilic material is breakable to at least partly enclose at least one hair, and an electrode surface for electrically stimulating the skin by driving current from the electrode surface through the hydrophilic material to the skin comprising the at least one hair.

14 Claims, 10 Drawing Sheets

(56) References Cited

U.S. PATENT DOCUMENTS

2015/0265830 A1\* 9/2015 Simon .................. A61N 1/0456
600/13

OTHER PUBLICATIONS

WIPO, European International Search Authority, International Search Report and Written Opinion dated Aug. 12, 2015 in International Patent Application No. PCT/EP2015/060660, 12 pages.

\* cited by examiner

STIMULATION ELECTRODE

BACKGROUND OF THE INVENTION

Field of the Invention

This invention pertains in general to the field of stimulation electrodes, and especially to stimulation electrodes for transcranial direct current stimulation comprising a hydrophilic material.

Description of the Prior Art

Transcranial direct current simulation (tDCS) is a form of neurostimulation which includes, for example, delivering a constant and low current directly to a brain region of a person, namely a subject, through electrodes. Commonly used today is that a low current is normally in a range of 0.5 mA to 2 mA. tDCS is useful, for example, for treating patients with brain injuries, such as strokes, for treating depression, anxiety, tinnitus, chronic pain, and for enhancing language and mathematical abilities, addressing attention span problem, for enhancing problem solving abilities, for improving memory, and for enhancing a coordination of body movements.

Known stimulation electrodes use conductive materials such as gels, spray or wet pads for creating better electrical contact between the electrode and a scalp of a patient. These known electrodes have the problem that a large amount of the conductive gel or similar need to be used in order to create a good electrical contact. This usually makes patients with a lot of hair uncomfortable and forces them to shower after the procedure to remove the conductive material from hair and the scalp. Additionally, these materials are hard to apply correctly in order to ensure a good contact between the electrode and the scalp. They are normally applied in a trial and error approaches were an operator uses a small amount and then places the electrode on the conductive material and testes the conduction. This is then repeated by adding more of the conductive material until a desired conductive result is achieved. This is a tiresome approach and takes a long time, resulting in additional stress for the operator and is an extra unknown factor that may stress the patient.

EP2055347 discloses that the purpose of the electrodes is that they possess components capable of indicating to an end user when the electrode is in need of replacement. In embodiments of EP2055347, an electrode of the present disclosure may include a substrate, and a conductive composition on at least a portion of a surface of the substrate, the conductive composition including at least one hydrogel and at least one pH indicator component which will change its color or opacity on exposure to a change in pH, thereby providing an indication to replace the electrode. Further, EP2055347 only discloses that the hydrogel is crosslinked to an adequate degree, the bulk hydrogel is strong enough, even when swelled with additional liquid, to provide adhesive support for pacing leads, thereby establishing extended connection of the lead to tissue. The electrodes disclosed in EP2055347 are electrodes for use with an electrocardiogram monitoring (EGG) machine, an electroencephalogram (EEG) machine, or a transcutaneous electrical nerve stimulation (TENS) machine. US2011/112605 discloses that some embodiments comprise a topical analgesic and/or anesthetic which is utilized in conjunction with surface electrodes to decrease discomfort related to excitation of superficial sensory nerves. In one implementation, a lidocaine (or similar, ex. capsaicin or other NSAID) paste or gel is manufactured into or layered below (skin contact side) of the hydrogel contact layer of the surface electrodes utilized during NMES. Thus, when electrodes make contact with the skin, the analgesic/anesthetic is automatically applied without extra steps for the operator. In variation embodiments, the topical analgesic/anesthetic is applied in discrete locations by an operator prior to placement of stimulation electrodes or a stimulation pad.

Thus, a need for an improved stimulation electrode solving the above problems is needed.

SUMMARY OF THE INVENTION

Accordingly, embodiments of the present invention preferably seeks to mitigate, alleviate or eliminate one or more deficiencies, disadvantages or issues in the art, such as the above-identified, singly or in any combination by providing a device according to the appended patent claims.

According to a first aspect of the invention a skin electrode for stimulation comprising a superporous hydrophilic material having a first relaxed state and a second expanded state. In the second expanded state the hydrophilic material is breakable for at least partly enclose at least one hair. The skin electrode further comprises an electrode surface for electrically stimulating skin by driving current from the electrode surface through the hydrophilic material to the skin comprising the at least one hair.

According to a second aspect of the invention a skin electrode for stimulation comprising a conductive electrode and an anaesthetic agent for arrangement between the conductive electrode and skin of a stimulation area of a patient.

According to a third aspect of the invention the use of an anaesthetic agent when performing electrical stimulation on skin of a patient for reducing sensation of the electrical stimulation.

Further embodiments of the invention are defined in the dependent claims, wherein features for the second and subsequent aspects of the invention are as for the first aspect mutatis mutandis.

Some embodiments of the invention provide for increased breaking apart of the superporous hydrophilic material.

Some embodiments of the invention provide for a better enclosing of a hair by the superporous hydrophilic material.

Some embodiments of the invention provide for reduced transfer loss from the electrode to the skin.

Some embodiments of the invention provide for reverting from the second expanded state to the first relaxed state of the superporous hydrophilic material.

Some embodiments of the invention provide for better penetration and/or conformation of the superporous hydrophilic material.

Some embodiments of the invention provide for a better distribution of the superporous hydrophilic material over the surface area of the electrode and consequently with a same area to the skin of the patient.

Some embodiments of the invention provide for the hydrophilic material to be contained within the electrode surface.

Some embodiments of the invention provide for the electrodes are preferably used for transcranial direct current stimulation.

Some embodiments of the invention provide for using higher currents when stimulating.

Some embodiments of the invention provide for the hydrophilic material to comprise the anaesthetic agent.

Some embodiments of the invention provide for less discomfort and/or pain and/or stress for a patient.

It should be emphasized that the term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

These and other aspects, features and advantages of which examples of the disclosure are capable of will be apparent and elucidated from the following description of examples of the present disclosure, reference being made to the accompanying drawings, in which.

DESCRIPTION OF THE PREFERRED EMBODIMENTS

Figure 1:
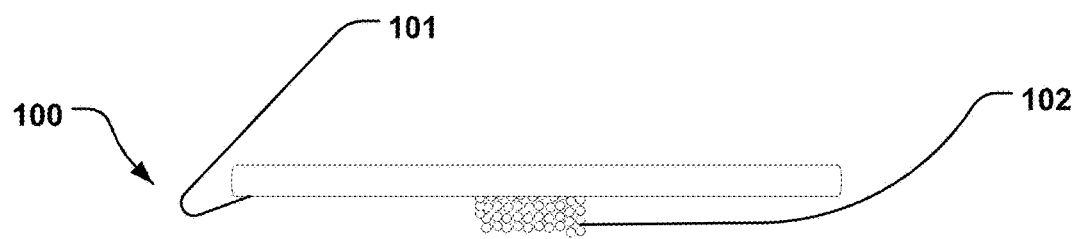
FIG. 1 is a side view of a schematic drawing of an electrode comprising superporous hydrophilic material.

Specific examples of the disclosure will now be described with reference to the accompanying drawings. This invention may, however, be embodied in many different forms and should not be construed as limited to the examples set forth herein. Rather, these examples are provided so that this disclosure will be thorough and complete, and will fully convey the scope of the invention to those skilled in the art. The terminology used in the detailed description of the examples illustrated in the accompanying drawings is not intended to be limiting of the invention. In the drawings, like numbers refer to like elements.

The following description focuses on an example of the present disclosure applicable to a skin stimulation electrode and in particular to skin stimulation electrode comprising a superporous hydrophilic material.

FIG. 1 illustrates a skin electrode 100 for stimulation comprising a superporous hydrophilic material 102. The superporous hydrophilic material 102 has a first relaxed state and a second expanded state. In the second expanded state the superporous hydrophilic material 102 is breakable for at least partly enclose at least one hair 103. The skin electrode 100 also comprises an electrode surface 101 for electrically stimulating skin 104 by driving current from the electrode surface 101 through the superporous hydrophilic material 102 to the skin 104 comprising the at least one hair 103 and which finally stimulates the brain in a desired way. By using the skin electrode 100 comprising superporous hydrophilic material 102, it is thereby possible to have the hydrophilic material 102 expanding by use of a fluid such as water, from the relaxed state to the expanded state, in which expanded state the material is breakable to at least partly enclose at least one hair 103 on the patient's skin. This allows the superporous hydrophilic material 102 to better cover a large area of skin around the hair and create a good contact between the skin 104 and the electrode surface 101 so that current is better transferred to the skin from the electrode surface 101, than any known electrodes as of today such as in prior art wherein hydrogels have only been used in combination with a PH-marker to disclose if the electrode comprising the hydrogel and the marker needed to be changed to a new electrode. The amount of superporous hydrophilic material 102 that is required to cover a size of the electrode surface 101 depends on the size of the electrode surface and the amount of expansion of the superporous hydrophilic material 102 from the first to the second state. In some examples, an amount of 5%-50% of the superporous hydrophilic material 102, in the first relaxed state, is required to substantially cover the electrode surface 101, in the second expanded state. The location of the superporous hydrophilic material 102 can be chosen to be anywhere on the electrode surface 101 but is preferably placed in a middle of the electrode surface 101, as seen in FIG. 1. In an examples the superporous hydrophilic material 102 comprises polymerized acrylamide, polymerized acrylic acid, polymerized sulfopropylacrylate potassium salt, polymerized methylene bisacrylamide, inter-penetrating network former crosscarmelose sodium salt.

Figure 2:
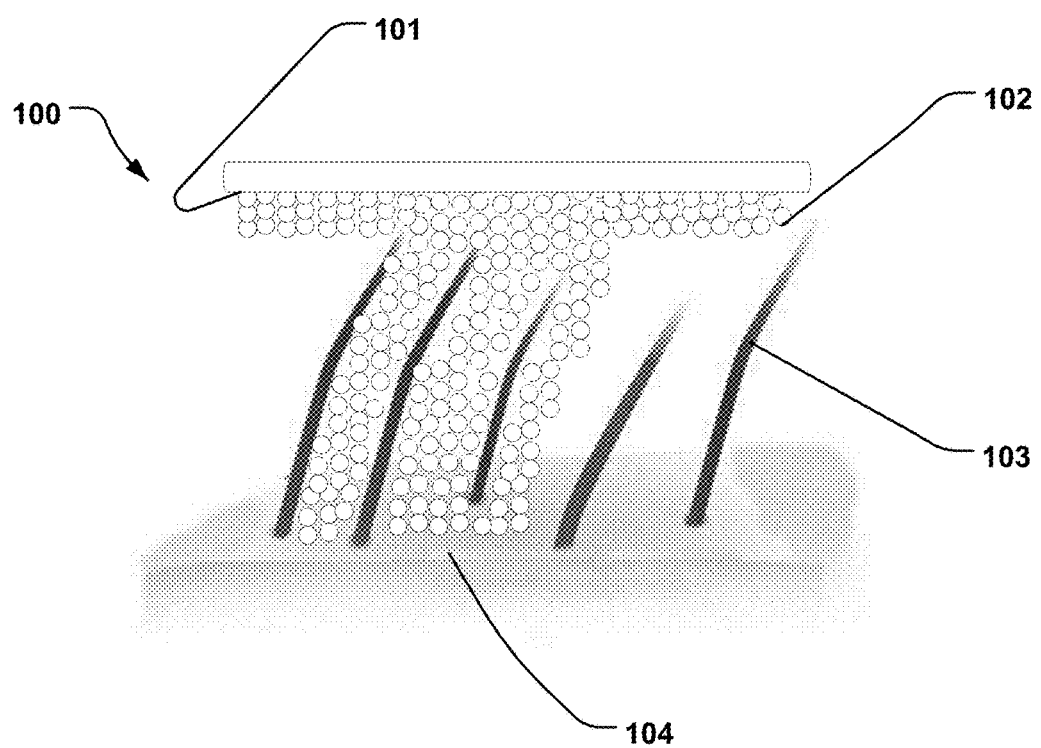
FIG. 2 is a side view of a schematic drawing an electrode comprising superporous hydrophilic material and a scalp with hair.

As illustrated in FIG. 2, this improved contact is due to the ability of the superporous hydrophilic material 102, when in its second expanded state, to break apart in a direction but stay connected in a direction extending between the skin 104 and the skin electrode surface 101, so that the superporous hydrophilic material 102 better penetrates between the hairs 103 and comes in contact with a larger surface of the skin 104. Because of high water content in the superporous hydrophilic material 102 and weakening of crosslinks and/or inter networks between pores within the superporous hydrophilic materials 102, the superporous hydrophilic material 102 breaks apart. Superporous hydrophilic materials 102 are generally characterized as relatively low strength, low modulus materials, smooth and having lubricious surfaces. Some of the more commonly employed methods to assess physical and mechanical properties of superporous hydrophilic material's 102 are examination of swelling behaviour, the equilibrium water content, tensile and compressive strength, diffusivity or mesh size and mass loss.

Superporous hydrophilic material 102 (porous hydrophilic crosslinked structures) have the ability to expand in aqueous environments up to 200-700 times their own weight in the dry state. The size, porosity, hydrophilicity and crosslink density are the major factors that control the swelling rate and swelling capacity of the superporous hydrophilic material 102. Depending on the application, the size and structural porosity of the superporous hydrophilic material 102 will be different. Superporous hydrophilic materials 102 are mostly characterized by their swelling and mechanical properties in different media. The swelling properties are measured by weight, volume and dimension at different time intervals (to obtain swelling rate) or at equilibrium (to obtain swelling capacity). In an example, the superporous hydrophilic material has a weight swelling ratio of at least 2 and/or the hydrophilic material has a volume swelling ratio of at least 2. By having a hydrophilic material with the weight swelling ratio of at least 2 and/or volume swelling ratio of at least 2, the superporous hydrophilic material 102 better breaks apart and thus creates a better enclosing of the hair 103. Preferably the expansion is in the range of 2-5 times in diameter in a single linear direction, calculated by use of Expansion=(Diameter wet)/(Diameter dry).

Since superporous hydrophilic materials 102 are mostly based on hydrophilic and ionic monomers, their swelling and mechanical properties are generally sensitive to the type and nature of the swelling medium and as swelling ratio increases mechanical strength tends to decrease. Ionic strength, pH, salts, organic solvents and pressure are the most important factors. The superporous hydrophilic material 102 swelling properties (measured by volume (VSR) or weight (WSR)) generally increase with an increase in pH, and decrease in ionic strength, salt concentration, cation valence and pressure. In an example, the hydrophilic material is configured to revert from the second expanded state to the first relaxed state by use of an acid. By having the superporous hydrophilic material 102 to be reversed from the expanded state to the relaxed state, the superporous hydrophilic material 102 can be re-used.

As discussed above, an increase in amount of crosslinks and/or an inter-network support structure increases the mechanical stability of the superporous hydrophilic material 102. In an example, the superporous hydrophilic material has a mechanical strength of at the most the strength of a hair, i.e. the compressional strength of the hair. When the superporous hydrophilic material 102 has at the most the mechanical strength of a hair, the superporous material breaks easier apart when contacting a hair exerting a counter force (compressional strength) against the superporous hydrophilic material, and thus creates an even better penetration and/or conformation of the superporous hydrophilic material 102 to the scuip/skin when pressed down by a user and/or the electrode itself, to the skin 104. In an example for achieving the desired mechanical strength the superporous hydrophilic material 102 comprises polymerized acrylamide 50.1%, polymerized acrylic acid 1.7%, polymerized sulfopropylacrylate potassium salt 36.2%, polymerized methylene bisacrylamide (serves as a bifunctional crosslinker) 0.9%, inter-penetrating network former crosscarmelose sodium salt 11.1%, or polymerized acrylamide 45.1%, polymerized acrylic acid 1.5%, polymerized sulfopropylacrylate potassium salt 32.6%, polymerized methylene bisacrylamide 0.8%, inter-penetrating network former crosscarmelose sodium salt 20.0%, or polymerized acrylamide 53.1%, polymerized acrylic acid 1.8%, polymerized sulfopropylacrylate potassium salt 38.3%, polymerized methylene bisacrylamide 0.9%, inter-penetrating network former crosscarmelose sodium salt 5.9%.

The impedance of an electrode is vital for its performance characteristics in a device for recording and/or stimulation applications. Conventional metal electrodes have relatively high impedance compared to other types of coated electrodes at 1 kHz. This is mainly due to the rough surface topography which increases the available charge transfer area on the electrode. In one example, an impedance of the superporous hydrophilic material is substantially the same as an impedance of the skin. By matching the impedance between the superporous hydrophilic material and the skin, any electrical transfer loss from the superporous hydrophilic material to the skin is minimised. The better the impedance between different interfaces is, i.e. the interfaces; electrode—superporous hydrophilic material 102, and superporous hydrophilic material 102—skin, the lower any electrical transfer loss is to the skin of the patient and thus less power is lost from a current source to the skin 104. Hence, preferably the superporous hydrophilic material is matched with both connecting surfaces, i.e. electrode surface and skin. Normally the skin impedance lies within 10k-1M ohm depending on where on the body the impedance is measured and more specifically for the skull and skin impedance, the impedance lies according to our tests at 0.4 mA at 10 kOhm, at 0.3 mA at 13 kOhm and at 0.1 mA at 18 kOhm.

Figure 3:
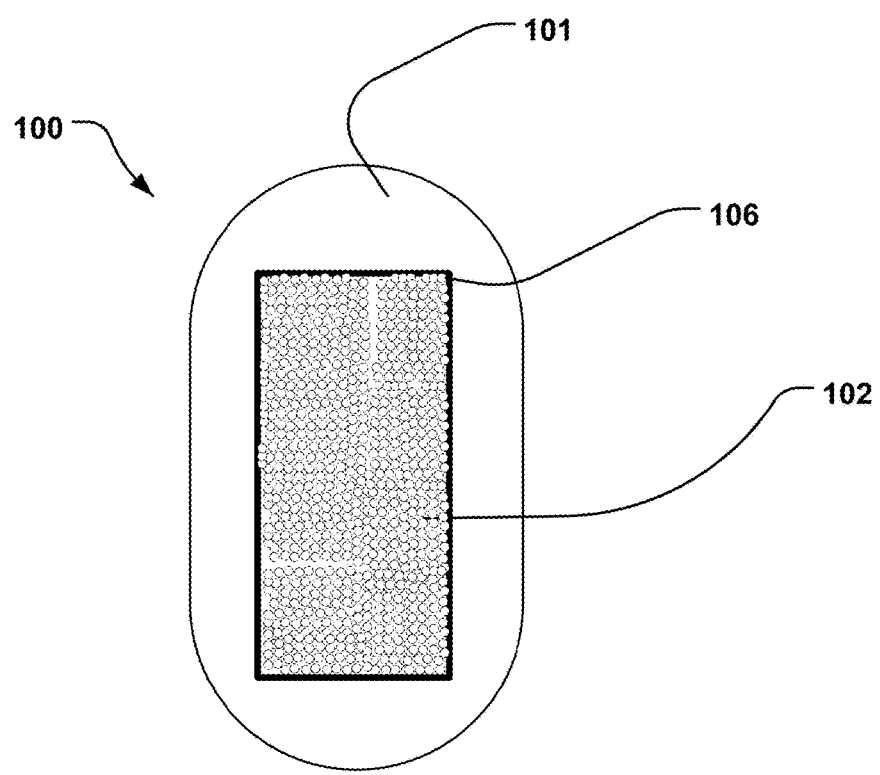
FIG. 3 is a front view of a schematic drawing of an electrode comprising superporous hydrophilic material and edges.

In an example, the hydrophilic material also conforms to a shape of the skin electrode. By having the shape of the superporous hydrophilic material match the shape of the electrode, the current is evenly distributed over the surface area of the electrode 101 and consequently substantially with the same area to the skin 104 of the patient. In another example, as illustrated in FIG. 3, the electrode surface 101 has at least one edge 106 for retaining the superporous hydrophilic material 102 in contact with the electrode surface 101 and the skin 104 of the patient. Even though 4 edges are illustrated in the figure less edges are possible. By having the electrode surface 101 comprising at least one edge 106 on the surface of the electrode 101, the superporous hydrophilic material 102 is mechanically restricted within the conductive surface of the electrode 101 and no superporous hydrophilic material 102 is leaked outside of the surface. This may improve patient comfort, amount of superporous hydrophilic material 102 that is used and/or better distribution of the superporous hydrophilic material 102 at the electrode surface which in turn gives a better electrical distribution.

In an example, the skin electrode for stimulation further comprising an anaesthetic agent. By having the electrode comprising the anaesthetic agent it is possible to apply higher currents to the skin of the patient since the patient will not feel any or as much discomfort as previously at the same currents without any agent. Compared to prior art wherein a combination of other types of hydrogel and anastethic agents have been used but were the hydrogel was more of solid hydrogel thus having the same problems as discussed above with worse electrical conduction to the skull/skin of the patient than with hydrogels of the current disclosure In another example, the superporous hydrophilic material 102 comprises the anaesthetic agent. By having the superporous hydrophilic material 102 comprising the anaesthetic agent it is only necessary to use one material on the electrode which speeds up the procedure and makes it easier for the user compared to having to apply two different components when using an electrode.

In an alternative example, a skin electrode for stimulation comprises a conductive electrode and an anaesthetic agent for a stimulation of an area of a patient. By having an anaesthetic agent more current can be used without discomfort for a patient than without any anaesthetic agent. For example, the anaesthetic agent is selected from a list of agents, the list comprises amylocaine, articaine, benzocaine, benzonatate, bupivacaine, butacaine, butanilicaine, chloroprocaine, cinchocaine, cocaine, dimethocaine, eucaine, etidocaine, hexylcaine, levobupivacaine, lidocaine, mepivacaine, meprylcaine metabutoxycaine, orthocaine, oxetacaine, oxybuprocaine, phenacaine, piperocaine, pramocaine, prilocaine, procaine, proparacaine, propoxycaine, quinisocaine, ropivacaine, trimecaine or tetracaine, and/or any combination thereof.

In one example, the use of an anaesthetic agent when performing electrical stimulation on skin of a patient for reducing sensation of the electrical stimulation. By using an anaesthetic agent more current can be used when stimulating the patient without additional discomfort for the patient.

The above described electrodes is in one example a part of a system which includes a power controller and at least two electrodes, where the two electrodes are positioned on a head region of a subject, for example a user, and connected to the power controller through wires. One of the electrodes is a positive electrode, i.e., an anode, and the other electrode is a negative electrode, i.e. a cathode. The power controller includes an electrode drive arrangement that generates electric signals for driving the anode and the cathode to cause transcranial stimulation of the head region of the subject. In an example, the power controller includes a power source for providing a constant low current to the anode, which flows through the skull and brain to the cathode, thereby creating a circuit. By "low current" in relation to transcranial direct current stimulation is meant currents of 20 milliAmperes (mA) or less. In an example, the electrode is adapted to apply a direct current of 0.5-5 mA. Additionally in another example, the skin electrode is configured to be used for and sized for transcranial direct current stimulation. This allows the electrode to be designed in such a way that it can be easily used on a skull of the patient and with materials that has fewer restrictions than electrodes that are used in the body of the patient.

In yet other alternative examples of an skin electrode, the skin electrode comprises a fluid access opening for separating said hydrophilic material and a fluid. The fluid access opening is openable for allowing hydrophilic material in contact with said fluid whereby said hydrophilic material assumes said second expanded state.

In an example the skin electrode comprises a fluid chamber having said fluid access opening and containing said fluid.

As discussed above, and now in greater detail a method of contacting (stimulating) skin with a skin electrode having an electrode surface and a superporous hydrophilic material having a first relaxed state and a second expanded state. The method comprises breaking the superporous hydrophilic material to at least partly enclose at least one hair in the second state to create contact between said electrode surface and said skin having the at least one hair. The user may in an example electrically stimulate the skin by driving current from the electrode surface through the hydrophilic material to the skin comprising the at least one hair.

Figure 5:
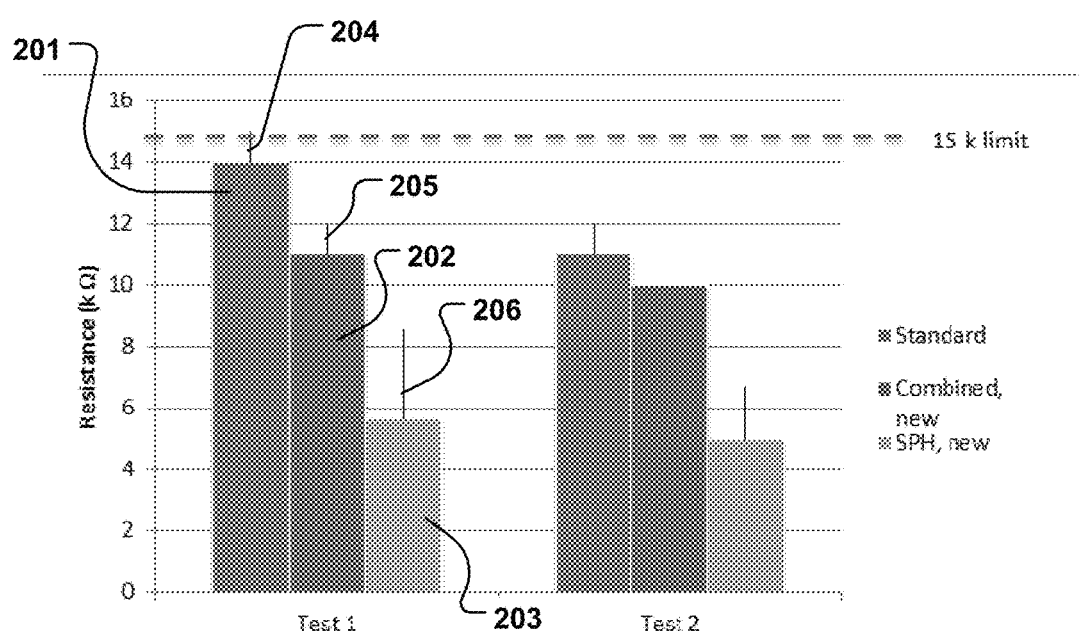
FIG. 5 is a chart view illustrating the result from experiment 1.

FIG. 5 illustrate the average resistance values and the standard deviations for all test subjects from experiment 1. The length of the staples corresponds to the value of the average resistance. The average resistance from the test result are measured by three parameters standard 201, combined 202, and SPH 203. The lines above the stables illustrates the standard deviations for the test result and the length of the lines corresponds to their values. The average standard deviation from the test result are measured by the parameters standard 204, combined 205 and SPH 206.

FIGS. 6a-l illustrate a second experiment that was carried out with a Sooma tDCS device. The second experiment aimed to test the resistance of samples of standard swell super porous hydrogel (SPH) in a cylinder volume. The lines from FIG. 6a-i with triangles corresponds to the measured voltage [V] values and the lines The lines from FIG. 6a-i with circles corresponds to the measured resistance [Ohm] values.

Following is further examples of devices and methods according to the disclosure above used in an experiment for evaluating contact quality with the superporous hydrogel (SPH) electrodes according to this disclosure compared to a standard carbon-silicon electrode design.

Experiment 1

The experiment was carried out with a Sooma tDCS device and three adult male subjects (#1, #2 and #3) participated in the study. Subject 1 was without any hair in the test area on the scalp and subject 2 and 3 had hair in the test area.

Electrodes

A standard silicon-carbon electrode (35 cm2 surface area) was used as reference and inserted into a sponge pouch soaked with 0.9% NaCl solution to provide improved electrical contact with subject scalp, as is a standard practice today when trying to improve conduction between a patient and an electrode.

Figure 4A:
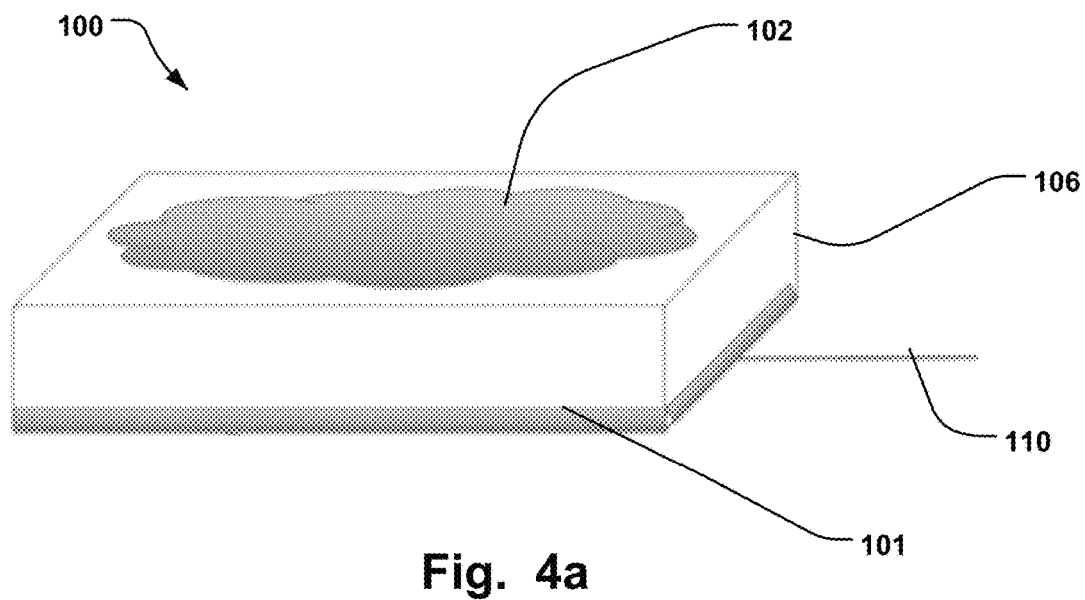
FIGS. 4a and 4b are side views of an electrode comprising edges and comprising a superporous hydrophilic material
Figure 4B:
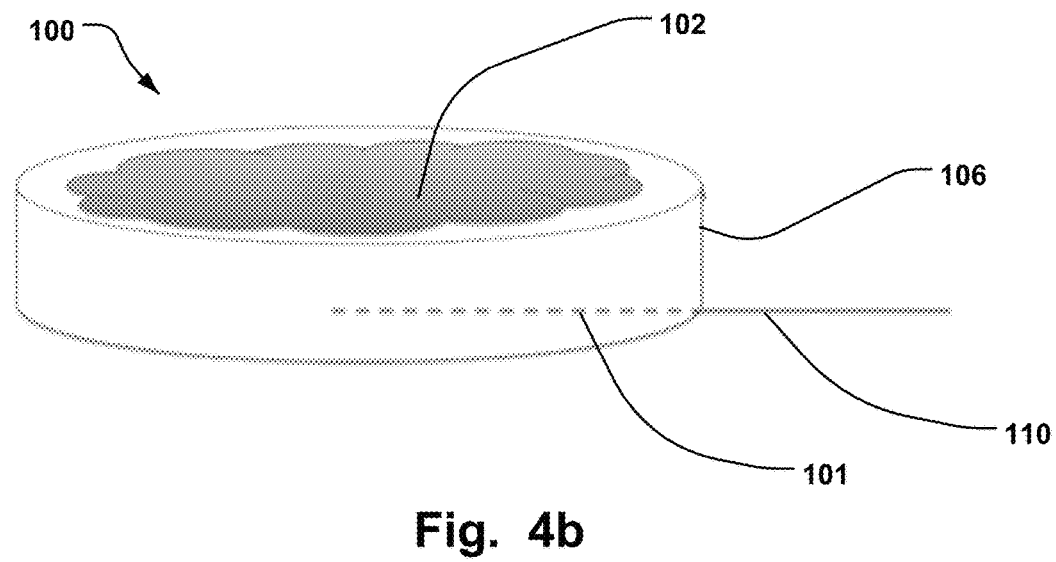

An example of an electrode 100 according to the disclosure is seen in FIG. 4a, wherein a non-conductive rim 106 is attached to a standard electrode with a conductive surface 101. The superporous hydrogel 102 is applied to a volume constrained by the electrode surface 101 and the non-conductive rim 106. An electrical cable 110 is connected to the electrode surface 101. Electrolyte (0.9% NaCl solution) was applied to the SPH to make it swell and the SPH absorbed all of the electrolyte solution and swelled to cover substantially the entire volume. The SPH and the electrolyte solution form a contact medium between the stimulation electrode and the subjects scalp. In another example of an electrode 100 according to the disclosure and as seen in FIG. 4b, the electrode 100 has a cup with diameter of 67 mm and surface area of 35 cm2 that is filled with low swelling SPH. Electrolyte (0.9% NaCl solution) is applied to the SPH and the SPH absorbs all of the electrolyte solution and essentially fills the entire volume. The SPH and the electrolyte solution form a contact medium between the stimulation electrode and the subject's scalp. An electrical cable 110 transfers current from a power source to the SPH.

Test Measurements

The experiment used the following method for each electrode design and test subject:

1. The electrode was attached to the subject scalp in frontal locations.
2. A 2 minute preparation time was used to let the electrolyte form a contact between the scalp and the electrode
3. A measurement of contact was carried out with 0.3 mA current. Contact measurement was carried out for 1 minute to let the electrode-skin interface to stabilize. (Test 1)
4. After the contact was below 15kΩ, the stimulator would let the operator to continue. The stimulation was started with 2 mA current
5. After one minute, the stimulation was set to pause and contact measurement was started again. The contact was let to stabilize for about 1 minute before measurement. (Test 2)

Results

Below are results from the two different tests in a tabular form for each subject and each electrode design.

|  | Test 1 (kΩ) | | | Test 2 (kΩ) | | |
| --- | --- | --- | --- | --- | --- | --- |
|  | Subject 1 | Subject 2 | Subject 3 | Subject 1 | Subject 2 | Subject 3 |
| Standard | 13 | 15 | 14 | 10 | 11 | 12 |
| Combined | 12 | 10 | 11 | 10 | 10 | 10 |
| SPH | 9 | 4 | 4 | 7 | 4 | 4 |

Below are reported average resistance values and standard deviations for all test subjects. FIG. illustrate a chart of the average resistance values and standard deviations for all test subject from experiment 1.

|  | Average resistance (kΩ) | | | Std. dev. (kΩ) | | |
|---|---|---|---|---|---|---|
|  | Standard | Combined | SPH | Standard | Combined | SPH |
| Test 1 | 14 | 11 | 5.67 | 1 | 1 | 2.87 |
| Test 2 | 11 | 10 | 5 | 1 | 0 | 1.73 |

Subject Sensations

The subjects were asked to compare the sensation experienced with the standard design to sensations experienced with the two new designs:
- Subject 1 found no noticeable effect with combined design. SPH reduced greatly the tingling feeling on the stimulation site.
- Subject 2 reported slight reduction in tingling with the combined design. SPH greatly reduced the tingling sensation.
- Subject 3 found no noticeable effect with combined design. SPH greatly reduced the tingling sensation.

Conclusions of the Experiment

SPH provides superior contact, transfer of current and subject comfort when compared to the standard silicone-carbon electrode. This is particularly clear when the contact area is covered with hair (Subjects 2 and 3). Internal resistance of the carbon-silicone electrode appears to diminish the improvements by the SPH, as is seen in the results for the "combined design".

Experiment 2

Another experiment was carried out with a Sooma tDCS device and to test resistance of samples of standard swell super porous hydrogel (SPH) in a cylinder volume, SPH as a pad and conventional electrodes. The composition of the SPH material used in this experiment, and in the other examples and/or experiments of the disclosure, is;

| Item | Content (% mass item/ mass hydrogel based on batch reaction composition) |
|---|---|
| Standard Superporous hydrogel | |
| Polymerized acrylamide | 50.1% |
| Polymerized acrylic acid | 1.7% |
| Polymerized sulfopropylacrylate potassium salt | 36.2% |
| Polymerized methylene bisacrylamide (note: serves as a bifunctional crosslinker) | 0.9% |
| Inter-penetrating network former crosscarmelose sodium salt | 11.1% |
| Measurement of diameter at dry state versus after swelling to equilibrium indicates a diameter change of 3.1X (Dwet/Ddry). Note this represents swelling only in a single linear dimension. | |
| Low-Swell Superporous hydrogel | |
| Polymerized acrylamide | 45.1% |
| Polymerized acrylic acid | 1.5% |
| Polymerized sulfopropylacrylate potassium salt | 32.6% |
| Polymerized methylene bisacrylamide (note: serves as a bifunctional crosslinker) | 0.8% |
| Inter-penetrating network former crosscarmelose sodium salt | 20.0% |
| Measurement of diameter at dry state versus after swelling to equilibrium indicates a diameter change of 2.5X (Dwet/Ddry). Note this represents swelling only in a single linear dimension. | |
| High-Swell Superporous hydrogel | |
| Polymerized acrylamide | 53.1% |
| Polymerized acrylic acid | 1.8% |
| Polymerized sulfopropylacrylate potassium salt | 38.3% |
| Polymerized methylene bisacrylamide (note: serves as a bifunctional crosslinker) | 0.9% |
| Inter-penetrating network former crosscarmelose sodium salt | 5.9% |

Measurement of diameter at dry state versus after swelling to equilibrium indicates a diameter change of 3.5X (Dwet/Ddry). Note this represents swelling only in a single linear dimension.

Figure 6A:
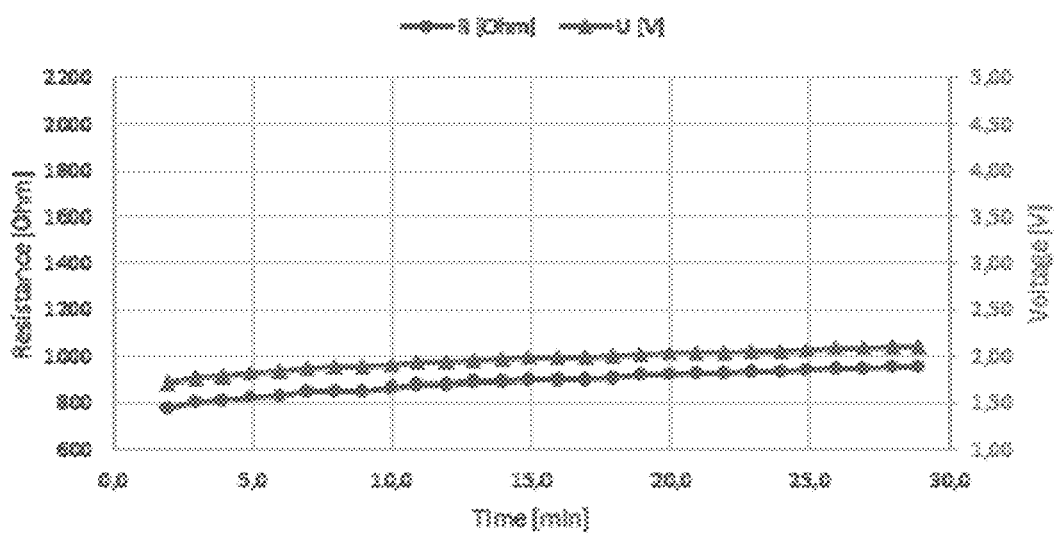
FIGS. 6a-i are chart views illustrating the results from experiment 2.
Figure 6B:
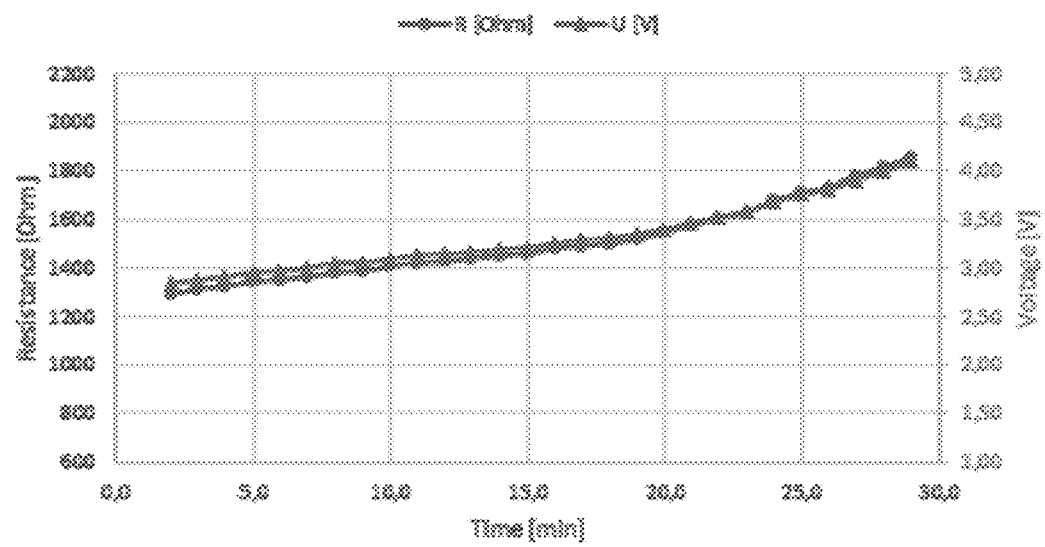
Figure 6C:
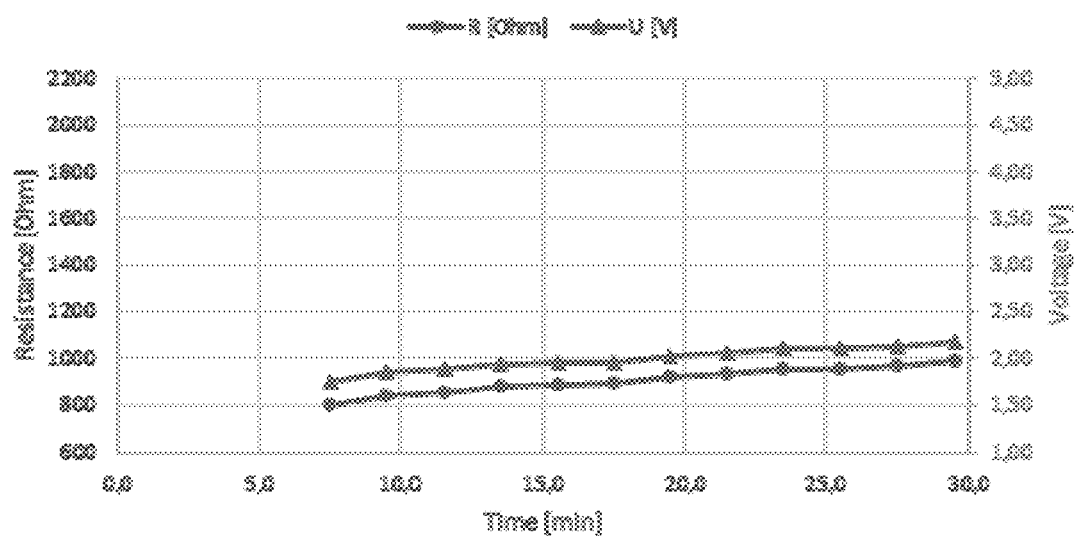
Figure 6D:
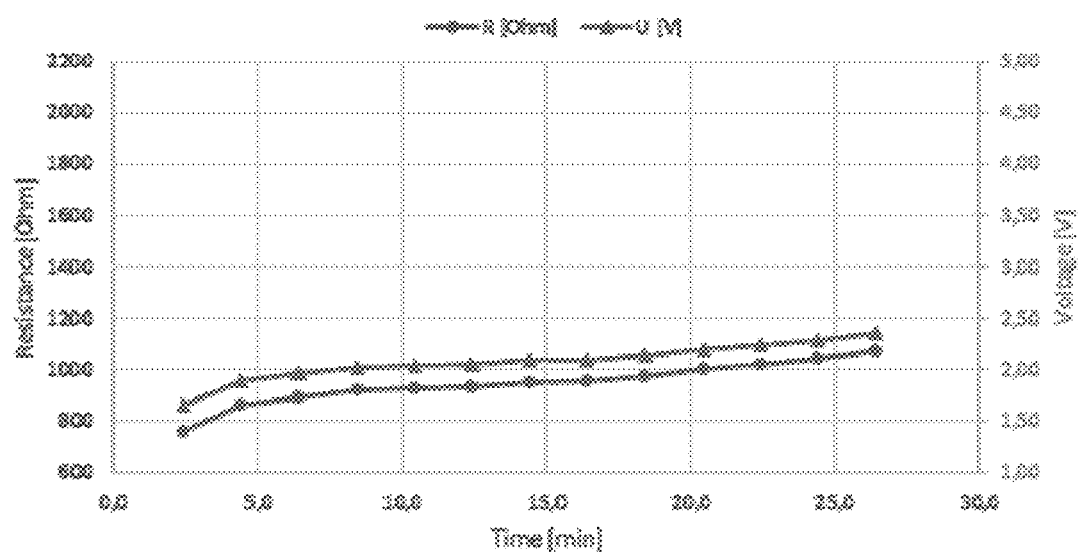
Figure 6E:
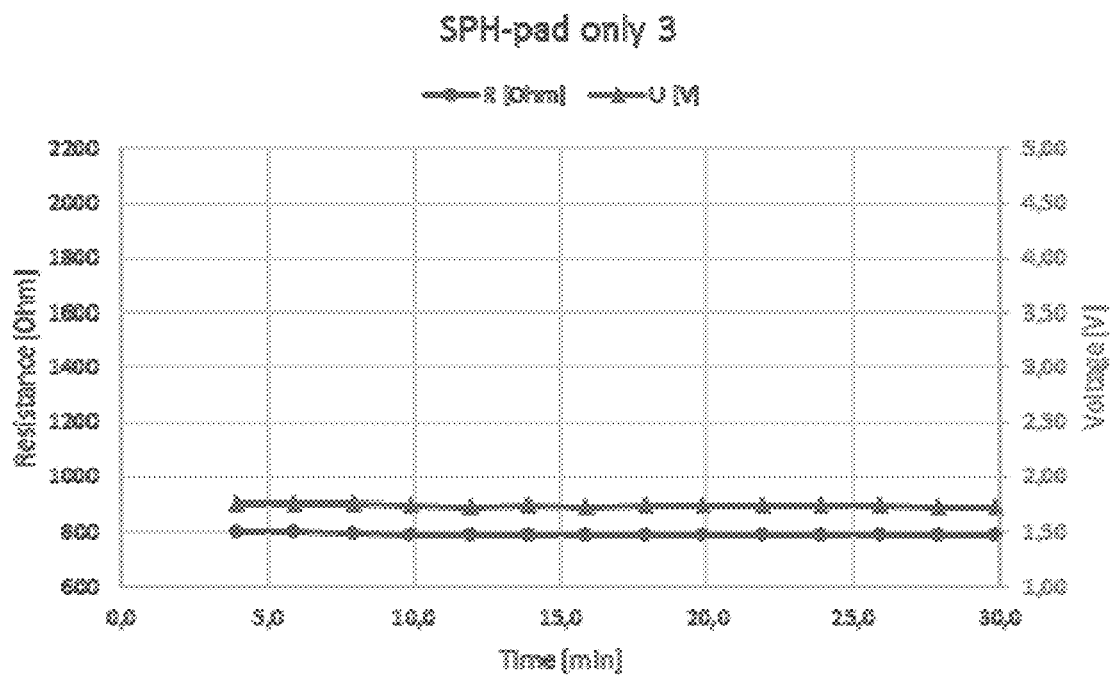
Figure 6F:
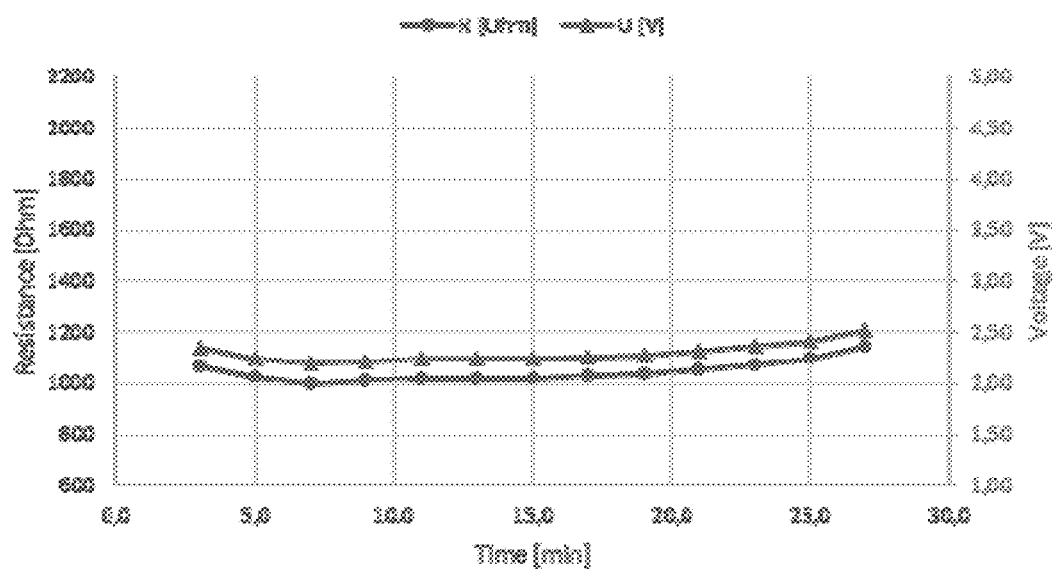
Figure 6G:
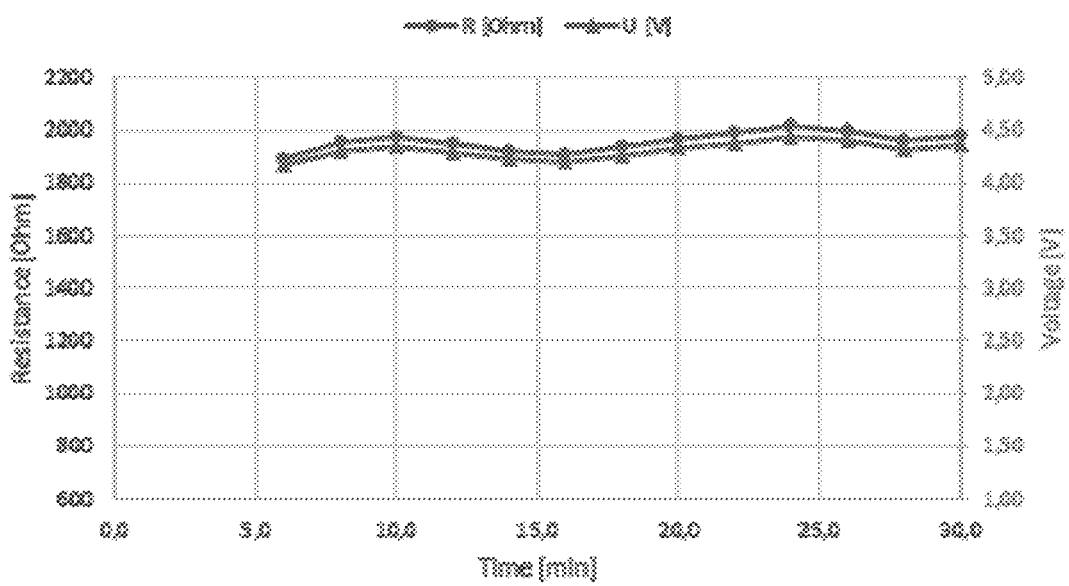
Figure 6H:
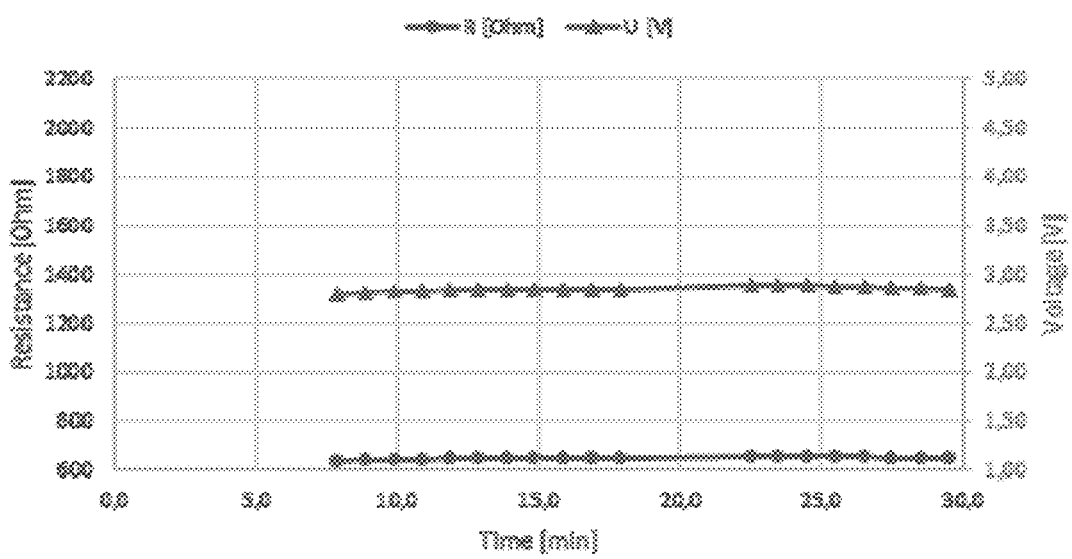
Figure 6I:
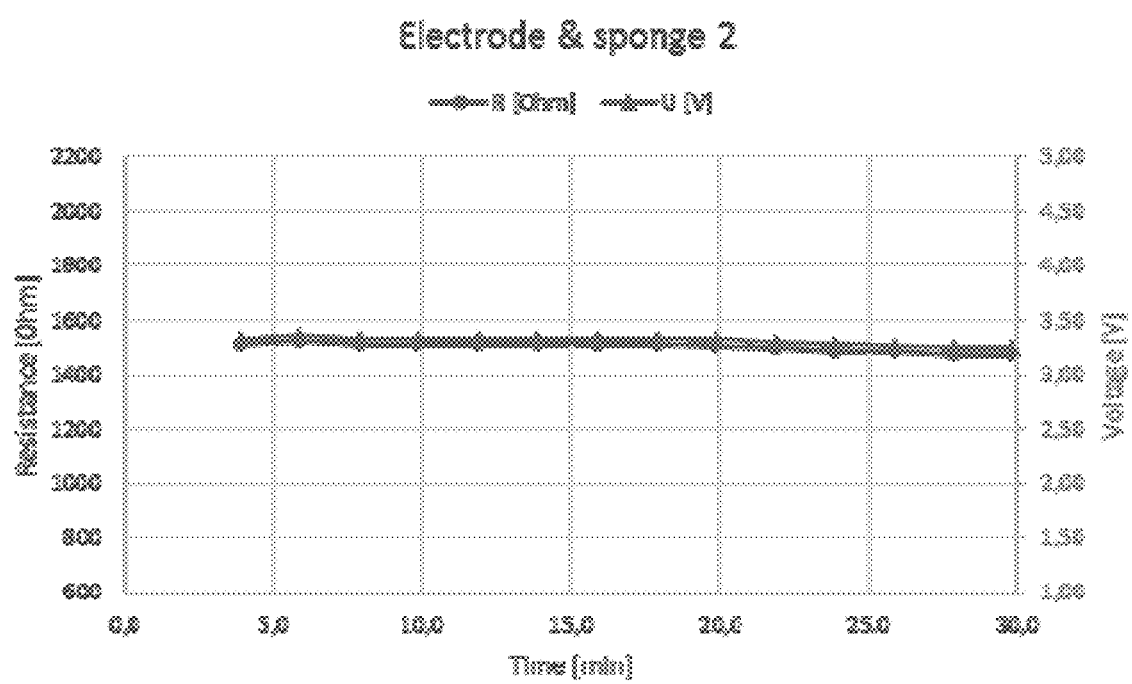

| Figure | Measurement | Voltage [V] MEAN ± STD (Over 30 min session) | RESISTANCE [Ω] MEAN ± STD (Over 30 min session) | RESISTIVITY [Ω · m] MEAN ± STD (Over 30 min session) |
|---|---|---|---|---|
| FIG. 6a | SPH standard swell cylinder 1 | 2.0 ± 0.11 | 891 ± 49 | 6.9 ± 0.37 |
| FIG. 6b | SPH standard swell cylinder 2 | 3.3 ± 0.35 | 1510 ± 161 | 6.9 ± 0.74 |
| FIG. 6c | SPH pad 1 (standard swell) | 2.0 ± 0.13 | 905 ± 88 | NA |
| FIG. 6d | SPH pad 2 (standard swell) | 2.1 ± 0.18 | 945 ± 83 | NA |
| FIG. 6e | SPH pad 3 (standard swell) | 1.7 ± 0.01 | 791 ± 4.5 | NA |
| FIG. 6g | SPH high swell cylinder | 4.3 ± 0.08 | 1960 ± 38 | 18.8 ± 0.36 |
| FIG. 6f | SPH low swell cylinder | 2.3 ± 0.09 | 1050 ± 41 | 6.5 ± 0.25 |
| FIG. 6h | Electrode & sponge* | 2.9 ± 0.03 | 647 ± 6.2 | NA |
| FIG. 6i | Electrode & sponge 2 | 3.3 ± 0.03 | 1500 ± 13 | NA |

As used herein, the singular forms "a", "an" and "the" are intended to include the plural forms as well, unless expressly stated otherwise. It will be further understood that the terms "includes," "comprises," "including" and/or "comprising," when used in this specification, specify the presence of stated features, integers, steps, operations, elements, and/or components, but do not preclude the presence or addition of one or more other features, integers, steps, operations, elements, components, and/or groups thereof. It will be understood that when an element is referred to as being "connected" or "coupled" to another element, it can be directly connected or coupled to the other element or intervening elements may be present. Furthermore, "connected" or "coupled" as used herein may include wirelessly connected or coupled. As used herein, the term "and/or" includes any and all combinations of one or more of the associated listed items.

The present disclosure has been described above with reference to specific examples and experiments. However, other examples than the above described are equally possible within the scope of the disclosure. Different method steps or a different order thereof than those described above may be provided within the scope of the disclosure. The different features and steps of the disclosure may be combined in other combinations than those described. The scope of the disclosure is only limited by the appended patent claims.

The invention claimed is:

1. A skin electrode for stimulation comprising; a superporous hydrophilic material having a first state and a second expanded state, in the second state the superporous hydrophilic material is breakable to at least partly enclose at least one hair, and an electrode surface for electrically stimulating the skin by driving current from the electrode surface through the hydrophilic material to the skin comprising the at least one hair,
wherein the superporous hydrophilic material comprises:
45.1% polymerized acrylamide,
1.5% polymerized acrylic acid,
32.6% polymerized sulfopropylacrylate potassium salt,
0.8% polymerized methylene bisacrylamide, and
20.0% inter-penetrating network former crosscarmelose sodium salt; or
the superporous hydrophilic material comprises:
50.1% polymerized acrylamide,
1.7% polymerized acrylic acid,
36.2% polymerized sulfopropylacrylate potassium salt,
0.9% polymerized methylene bisacrylamide, and
11.1% inter-penetrating network former crosscarmelose sodium salt; or
the superporous hydrophilic material comprises:
53.1% polymerized acrylamide,
1.8% polymerized acrylic acid,
38.3% polymerized sulfopropylacrylate potassium salt,
0.9% polymerized methylene bisacrylamide, and
5.9% inter-penetrating network former crosscarmelose sodium salt.

2. A skin electrode for stimulation according to claim 1, wherein the superporous hydrophilic material is breakable due to breakable crosslinks in the superporous hydrophilic material.

3. A skin electrode for stimulation according to claim 1, wherein the hydrophilic material has a volume swelling ratio of at least 2.

4. A skin electrode for stimulation according to claim 1, wherein an impedance of the hydrophilic material is substantially the same as an impedance of the skin.

5. A skin electrode for stimulation according to claim 1, wherein the hydrophilic material is configured to revert from the second expanded state to the first relaxed state by use of an acid.

6. A skin electrode for stimulation according to claim 1, wherein the hydrophilic material has a mechanical strength of at the most a mechanical compressional strength of hair.

7. A skin electrode for stimulation according to claim 1, wherein the hydrophilic material also conforms to a shape of the skin electrode.

8. A skin electrode for stimulation according to claim 1, wherein the electrode surface has at least one edge for retaining the hydrophilic material in contact with the electrode and the skin.

9. A skin electrode for stimulation according to claim 1, wherein the electrode is adapted to apply a direct current of 0.5-5 mA.

10. A skin electrode for stimulation according to claim 1, further comprising an anaesthetic agent.

11. A skin electrode for stimulation according to claim 1, wherein the hydrophilic material comprises the anaesthetic agent.

12. A skin electrode for stimulation according to claim 1, wherein the skin electrode is configured to be used and sized for transcranial direct current stimulation.

13. A skin electrode for stimulation comprising; a conductive electrode,
a superporous hydrophilic material having a first state and a second expanded state, in the second state the superporous hydrophilic material is breakable to at least partly enclose at least one hair, and an anaesthetic agent for arrangement between the superporous hydrophilic material and skin of a stimulation area of a patient,
wherein the superporous hydrophilic material comprises:
45.1% polymerized acrylamide,
1.5% polymerized acrylic acid,
32.6% polymerized sulfopropylacrylate potassium salt,
0.8% polymerized methylene bisacrylamide, and
20.0% inter-penetrating network former crosscarmelose sodium salt; or
the superporous hydrophilic material comprises:
50.1% polymerized acrylamide,
1.7% polymerized acrylic acid,
36.2% polymerized sulfopropylacrylate potassium salt,
0.9% polymerized methylene bisacrylamide, and
11.1% inter-penetrating network former crosscarmelose sodium salt; or
the superporous hydrophilic material comprises:
53.1% polymerized acrylamide,
1.8% polymerized acrylic acid,
38.3% polymerized sulfopropylacrylate potassium salt,
0.9% polymerized methylene bisacrylamide, and
5.9% inter-penetrating network former crosscarmelose sodium salt.

14. A skin electrode for stimulation according claim 13, wherein the anaesthetic agent is selected from a list comprising amylocaine, articaine, benzocaine, benzonatate, bupivacaine, butacaine, butanilicaine, chloroprocaine, cinchocaine, cocaine, dimethocaine, eucaine, etidocaine, hexylcaine, levobupivacaine, lidocaine, mepivacaine, meprylcaine metabutoxycaine, orthocaine, oxetacaine, oxybuprocaine, phenacaine, piperocaine, pramocaine, prilocaine, procaine, proparacaine, propoxycaine, quinisocaine, ropivacaine, trimecaine or tetracaine, and/or any combination thereof.

* * * * *